(12) United States Patent
Carol et al.

(10) Patent No.: US 8,409,070 B2
(45) Date of Patent: Apr. 2, 2013

(54) BRACHYTHERAPY APPARATUS AND METHOD FOR USE WITH MINIMALLY INVASIVE SURGERIES OF THE LUNG

(75) Inventors: Mark P. Carol, Burlingame, CA (US);
James E. Jervis, Atherton, CA (US);
Paul A. Lovoi, Saratoga, CA (US)

(73) Assignee: Xoft, Inc., Sunnyvale, CA (US)

( * ) Notice: Subject to any disclaimer, the term of this patent is extended or adjusted under 35 U.S.C. 154(b) by 1558 days.

(21) Appl. No.: 11/978,147

(22) Filed: Oct. 26, 2007

(65) Prior Publication Data

US 2009/0112047 A1    Apr. 30, 2009

(51) Int. Cl.
*A61N 5/00*    (2006.01)
(52) U.S. Cl. .......................................................... 600/3
(58) Field of Classification Search ............... 600/1–8
See application file for complete search history.

(56) References Cited

U.S. PATENT DOCUMENTS

| | | | |
|---|---|---|---|
| 5,797,948 A * | 8/1998 | Dunham | 606/194 |
| 5,931,774 A * | 8/1999 | Williams et al. | 600/2 |
| 6,413,204 B1 | 7/2002 | Winkler et al. | |
| 7,413,539 B2 * | 8/2008 | Lubock et al. | 600/3 |
| 2004/0087827 A1 * | 5/2004 | Lubock | 600/3 |
| 2005/0137714 A1 | 6/2005 | Gonzalez et al. | |
| 2006/0025815 A1 * | 2/2006 | McGurk et al. | 606/213 |
| 2007/0016179 A1 | 1/2007 | Francescatti et al. | |
| 2008/0009658 A1 | 1/2008 | Smith et al. | |
| 2008/0009659 A1 | 1/2008 | Smith et al. | |

OTHER PUBLICATIONS

Turner, Ph.D., CHP, James E., "Atoms, Radiation, and Radiation Protection", Second Edition, 1995, Section 2.10, pp. 40-45, John Wiley & Sons.

* cited by examiner

*Primary Examiner* — Christine Matthews
(74) *Attorney, Agent, or Firm* — Loginov & Associates, PLLC; William A. Loginov

(57) ABSTRACT

Brachytherapy treatment of a patient's lung tissue following resection is effected using a balloon applicator which is inserted, normally through the same opening used for the surgery, through the chest wall and into the cavity. The lung and chest openings are closed around the applicator and generally sealed around the applicator. A suction port is provided, in a suction circuit of the applicator, to withdraw fluid from the pleural cavity, at intervals as needed, to assure that the lung can be inflated. Different embodiments of suction circuits are disclosed. A bronchial applicator and method are also disclosed.

11 Claims, 4 Drawing Sheets

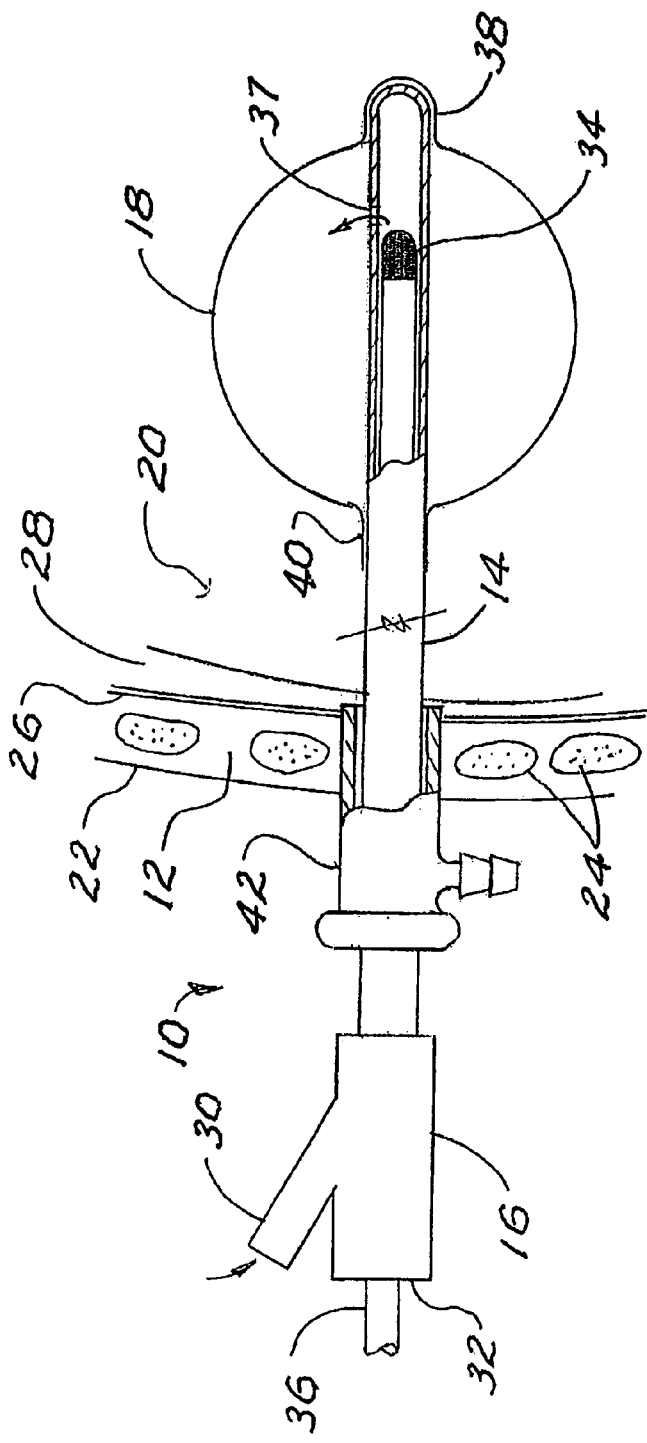
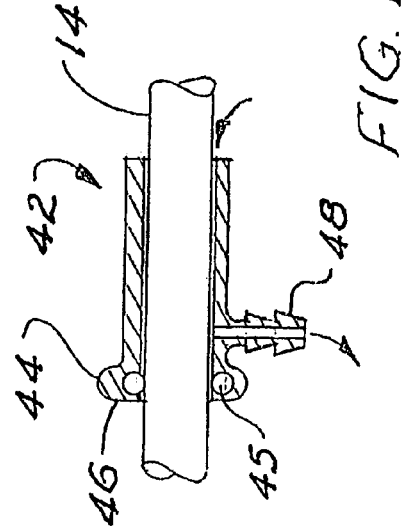
FIG. 1A
FIG. 1B

BRACHYTHERAPY APPARATUS AND METHOD FOR USE WITH MINIMALLY INVASIVE SURGERIES OF THE LUNG

BACKGROUND OF THE INVENTION

This invention pertains to minimally invasive surgery of the lung. In particular, it applies to application of brachytherapy techniques directed primarily to lung or pleural tissue surfaces exposed by or created as a result of tumor resection or the presence of primary cancer of the pleura. As with other tumor resection procedures, and even when pathology shows "clear" margins, there is potential for disease recurrence from diffuse proliferative disease in the resected surfaces. Balloon brachytherapy as an adjuvant follow-up to resection has been shown to reduce the likelihood of such recurrent disease.

Recent advances in surgical treatment of proliferative diseases of the lung include endoscopic procedures conducted through, and directed to lesions near the bronchi, and alternatively, video-assisted, minimally-invasive thoracic surgery directed to more peripheral disease and performed through incisions providing access to the thoracic cavity.

Today with early stage carcinoma of the lung, particularly in peripheral portions of the lung, treatment consists of resecting a wedge-shaped portion of lung through small incisions between adjacent ribs. If a wedge resection is inadequate to excise the entirety of the tumor, a lobectomy may be performed, removing a complete pulmonary lobe. Visualization is provided by camera or conventional fiber optic means mounted on a thoroscope and monitor display, although other state-of-the-art modalities can be used. Percutaneous or other methods or small incisions are used to introduce the necessary instrumentation, and with newer, minimally invasive techniques, conventional rib spreading is not required. The absence of rib spreading greatly reduces pain and hastens patient recovery, but narrows instrument access to a few small, discrete points on the rib cage. In order to provide adjuvant brachytherapy, methods and apparatus are needed that are compatible with the methods described above, and preferably without requiring additional access beyond that already established during resection.

With the intrabronchial approach to treatment of obstructions or lesions, a flexible bronchoscope with a working channel is generally employed in the affected bronchus while the remaining bronchial tree provides intraoperative ventilation. The bronchoscope also comprises either camera or fiber optic means to provide monitor display. Other instrumentation, preferably including that for follow-up brachytherapy, must be flexible, and of appropriate diameter for operation from within the working channel in order to be compatible. Extra or intrabronchial procedures often involve removal of a diseased section of bronchus, after which the exposed ends are usually approximated, either by suture or staple methods. Adjuvant brachytherapy may also be indicated after extra or intrabronchial surgery.

Brachytherapy practice traditionally comprises positioning a radiation source within target tissue and delivering a therapeutic dose of radiation, often from within a balloon, without overdosing either target or adjacent tissue. One particularly useful class of radiation sources are miniature electronic x-ray tubes which may be switched on and off at will, or which can be modulated with respect to either penetration depth (by controlling acceleration voltage of the x-ray tube) or dose intensity (by controlling filament current). These tubes are usually mounted at the end of a power supply cable and can emit isotropically or can be directional, emitting through a predetermined solid angle. One reference describing the principles and construction of such tubes is *Atoms, Radiation and Radiation Protection*, Second Edition, John E. Turner, Ph.D., CHP, 1995, John Wiley & Sons, Section 2.10. By contrast, isotope sources cannot in principle be modulated, and in addition require both isolation of the patient during radiotherapy and special facilities and apparatus to assure safety of personnel.

A minimum therapeutic absorbed dose (the prescription dose) is selected by the therapist to be delivered to all of the target tissue. Because dose generally decreases exponentially with distance from the source, accurate dose delivery is complicated and automated treatment planning is generally employed to assure delivery of a dose to the target tissue which is at least equal to the prescription dose, but which is also within allowable limits, thus avoiding substantial necrosis of normal tissue. The prescription dose may of necessity vary depending on the proximity of the source to radiation sensitive structures within the anatomy. Examples would include the skin, heart or other organs, and bone. Treatment planning is usually automated based on known radiation source parameters, prescription parameters, and geometry as determined by conventional imaging of the apparatus within tissue. Planning usually precedes the treatment delivery.

A useful device for controlling radiation intensity is an applicator, preferably a balloon applicator. Balloon applicators generally determine the interior shape of the target tissue (the resection cavity) and position the radiation source at a controlled distance from the tissue to be treated, thus defining treatment geometry and reducing the radiation intensity exponentially from spatial considerations. Several other means are available to moderate the absorbed dose delivered to the tissue. As noted above, the acceleration voltage applied to the x-ray tube can be used to limit the penetration depth of the radiation. The filament current can be reduced to lower emitted intensity, or in fact, to eliminate emissions altogether. Once output emission characteristics are determined by selection of x-ray tube input parameters, shielding can be used to reduce radiation intensity, or to control the direction of emissions, statically or dynamically as therapy progresses. Such shielding and attenuation methods for x-ray tubes are described in copending application Ser. Nos. 11/385,255, 11/471,277 and 11/471,013, each of which is incorporated herein in their entirety by reference.

Balloon applicators are known, for example those described in U.S. Pat. No. 6,413,204. In general, such applicators comprise a balloon mounted on a shaft proximate the distal end of the shaft, and further comprise at least one source guide to position the source at a known distance or distances from the balloon (and tissue cavity) surface. Fluid circuits can be provided communicating from outside the patient to the interior of the balloon for inflation purposes, or to outside the shaft and/or balloon for example for suction purposes or administration of anesthetic or therapeutic agents.

SUMMARY OF THE INVENTION

After a lung wedge resection or lobectomy, and preferably after pathology determination of clean margins, adjuvant brachytherapy may be indicated. If so, an applicator with a balloon is positioned within the resection cavity as the lung is closed, but before the chest cavity is closed, with the applicator shaft extending outside the patient. (Optionally, the skin may be closed as well, but it may be desirable to close the skin later such that pleural access is available for suturing or stapling after removal of the brachytherapy apparatus.) For this minimal access resection method (usually between the ribs), a substantially rigid applicator shaft is likely preferred. The balloon is then inflated. If necessary to close the lung effectively, the bronchoscopic methods of U.S. Patent Application Publication No. 2005/0137714 may be employed.

Once the balloon is properly positioned and inflated, the lung will likely self-expand or may be gently inflated. If desired, the chest may be imaged using conventional or state-of-the-art methods to assure that the lung tissue closely conforms to and surrounds the balloon as closely as possible. Advantageously, a fluid suction circuit in the applicator leading from outside the patient to outside the shaft of the applicator in communication with the pleural cavity is helpful for preventing or reducing pneumothorax, and facilitating proper lung inflation. The port intended to open into the pleural cavity is preferably adjustable along the shaft of the applicator such that it may be properly positioned and suction can be applied as desired. Alternatively, the suction circuit can comprise a valve, and/or the circuit can be used to instill therapeutic agents.

When the apparatus is properly situated and the anatomy is in conformance with the balloon, imaging of the site can be performed, and the information used to help create the treatment plan. Such information can include the shape of the treatment cavity, and the location of the cavity relative to anatomical structures, some of which could lie within the range of target tissue, or by their anatomical position, be at risk of inadvertent exposure during delivery of the prescription. If the latter occurs, radiation sensors capable of communication with the central controller can be applied to the skin, or positioned adjacent such structures by needle means or implanted during the surgical procedure. Output from these sensors can be used to eliminate over-exposure to radiation—inadvertent or otherwise.

The source, preferably mounted on a power cable or catheter, can then be inserted into the source guide, properly positioned, and optionally manipulated within or proximate the balloon to deliver the prescribed dose. Such manipulation can be manual, or is preferably automated in accordance with the treatment plan. The treatment plan may be delivered intraoperatively in its entirety, or may be delivered in fractions over time, in accordance with the treatment plan. At completion of treatment, the apparatus is removed from the body.

For application of brachytherapy after a bronchial resection or for treatment/palliation of an inoperable lesion (cancer), an applicator with a flexible shaft is advanced through the working channel of the bronchoscope. Once properly situated within a bronchus, the balloon is inflated, positioning the source guide accurately relative to the tissue to be treated. The source can then be positioned and radiotherapy begun. Because of the tubular nature of the resection, radiation delivery may be from within one positioning of a relatively short balloon with the source position fixed or translated within the balloon, or can be delivered from successive balloon positions with iterations of inflation, radiation, and deflation. Alternatively, an elongated or sausage-shaped balloon may be used. Because of the limited diameter of the bronchus, the methods and apparatus of co-pending U.S. application Ser. No. 11/925,200, have applicability here, and this teaching is incorporated herein in its entirety by reference.

The apparatus and methods of this invention may be employed to facilitate adjuvant brachytherapy used in conjunction with the procedures described above. The features and elements disclosed may be combined in other embodiments as will occur to those of skill in the art, but these variations are to be considered within the scope of the invention.

DESCRIPTION OF THE DRAWINGS

FIG. 1A is a schematic side view in partial section of an applicator of the invention passing through the skin and chest wall of a patient and extending into a lung.

FIG. 1B is a detail of the apparatus of FIG. 1A showing a suction sleeve with its open end positioned just within the pleural cavity of a patient.

DESCRIPTION OF PREFERRED EMBODIMENTS

Figure 2A:
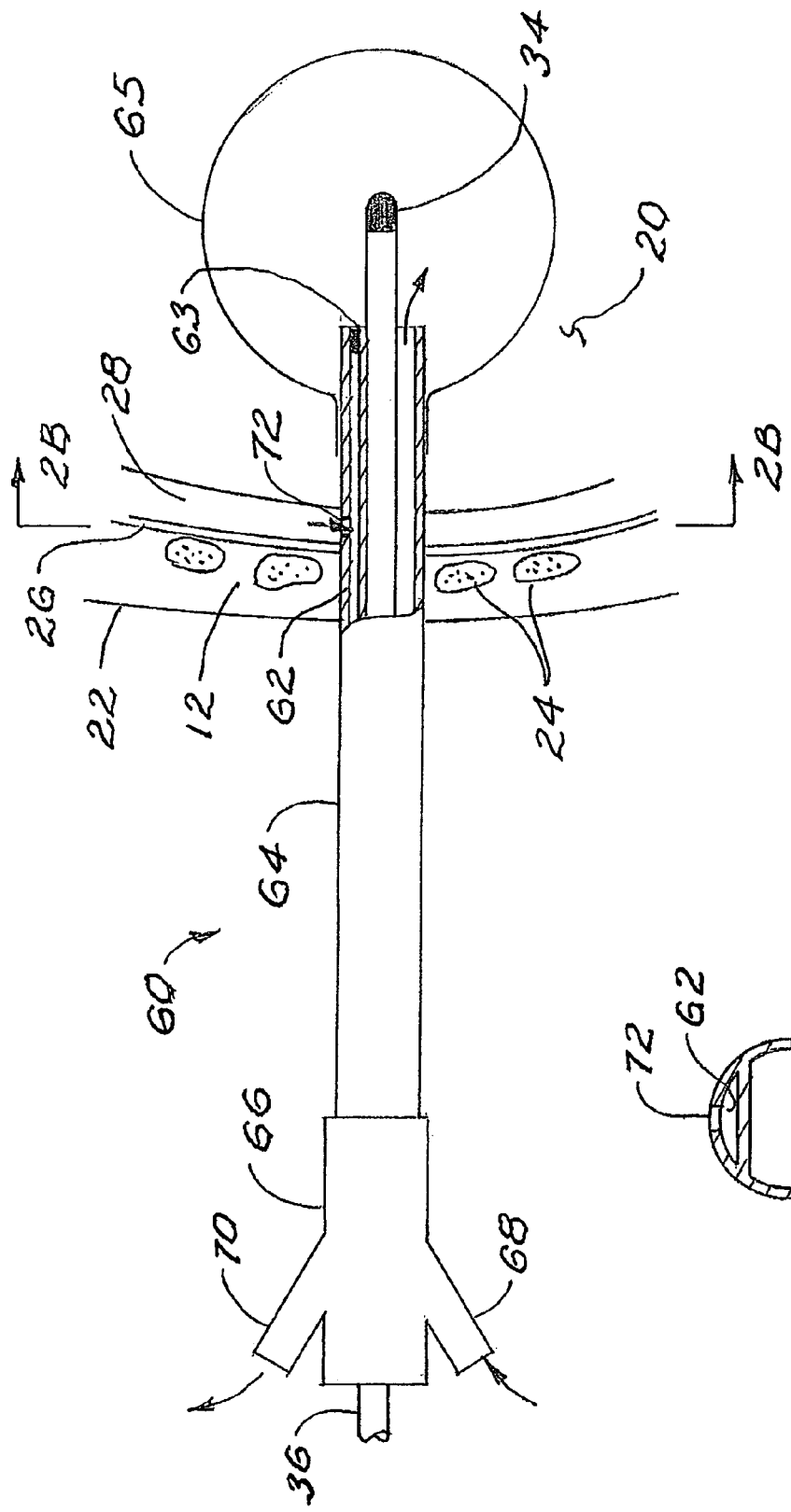
FIG. 2A is a schematic side view in partial section of an alternate applicator of the invention comprising a channel of a suction circuit within the applicator shaft bore, the channel having a port opened to communicate with the volume of the pleural cavity.

FIG. 1A is a side view in partial section showing an applicator 10 of the invention passing through the chest wall 12 of the patient. The shaft 14 of the applicator extends from a conventional hub 16 outside the patient into a balloon 18 positioned within a resected portion of the lung 20. The chest wall 12 includes the skin 22, ribs 24, and parietal pleura 26. The space between the parietal pleura 26 and the visceral pleura (not shown) covering the lung 20 defines the pleural cavity 28.

The hub 16 of the applicator 10 includes a side port 30 for inflating the balloon 18 and a central port 32 for advancing a radiation source 34 and source catheter 36 into the balloon 18. The central port includes a conventional seal (not shown) to avoid fluid leaks around the catheter through the hub. The shaft 14 extends from the hub into the balloon, and the balloon inflation medium passes through the shaft around the catheter 36 to a port 37 opening into the interior of the balloon 18 (see flow arrows). The interior of the shaft serves as a source guide, and accurately positions the source 34 within the balloon. Preferably the balloon is fastened to the shaft at both its distal end 38 and proximal end 40.

A suction sleeve 42 is located coaxially and slideably over the applicator shaft 14 as shown in FIG. 1B, just distal of the hub 16, and comprises a knob 44, a conventional seal 45 therein at its proximal end 46, sealing the interior of the sleeve 42 and outside of the shaft. A suction port 48 is provided near the proximal end, and in communication with the annulus between the sleeve 42 and the shaft 14. In use, the applicator 10 is advanced into the anatomy until the balloon 18 is properly positioned in the target tissue, i.e. in a resected portion of the lung. The sleeve is then slid on the shaft until the distal end is just within the pleura and in communication with the pleural cavity. If desired, apparatus for locking the sleeve position axially on the shaft may be provided, for example a locking nut or set screw (not shown). Thus upon application of suction, the pleural cavity 28 is drained and/or evacuated, facilitating expansion of the lung 20.

As an alternative to the shaft being attached to both the proximal and distal extremities of the balloon as depicted in FIG. 1A, the shaft need only communicate with the interior of the balloon as shown in FIG. 2A. The shaft 64 can extend into the volume of the balloon 65 and stop. The inflation medium passes from the port 68 into and through the annulus between the interior of the shaft 64 and the outside of the catheter 36 and into the interior of the balloon.

Figure 2B:
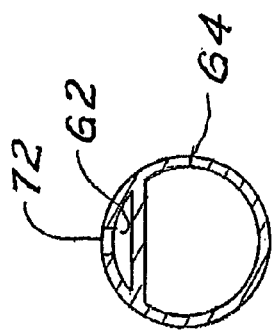
FIG. 2B is a section view of the applicator shaft of FIG. 2A showing the suction channel.

In the alternate applicator 60 of FIG. 2A, there is no suction sleeve as in FIG. 1A, but rather a suction channel 62 within the bore of the shaft 64. The channel 62 is shown in section view in FIG. 2B taken at the port 72. Again as in FIG. 1A, the chest wall 12 includes the skin 22, ribs 24, and parietal pleura 26. The space between the parietal pleura 26 and the visceral pleura covering the lung 20 defines the pleural cavity 28. The balloon 65 of this embodiment is only secured to the shaft 64 at the balloon proximal end. This fastening is shown as an alternate to the preferred fastening at both distal and proximal extremities of the balloon 65 as shown in FIG. 1A. The hub 66 of this embodiment comprises one port 68 for balloon inflation as described above in connection with FIGS. 1A and 1B, and a suction port 70 in communication with the suction channel 62 in the shaft 64 and the port 72. The distal end of the channel 62 is blocked (for example with a plug 63) so as not to communicate with the interior of the balloon. In use, and maintaining the sterile surgical field, the balloon is positioned properly within the resected tissue, and the axial location of the pleural cavity 28 is marked on the shaft over the suction channel 62. The applicator is then withdrawn from the anatomy sufficiently for the practitioner to pierce or cut a port 72 into the suction channel at the mark. Once the port is made, the applicator is reinserted into the anatomy so the port 72 communicates with the pleural cavity 28, the balloon 65 is inflated, and the source 34 and the source catheter 36 are inserted to commence radiation treatment. Suction may then be applied to the suction channel 62 via the hub suction port 70, thus draining the pleural cavity 28 of any fluid therein.

Alternatively, the suction channel 62 may have a long slot (not shown) communicating outside the shaft 64 in the manner of the port 72, but extending from the hub 66 distally and stopping short of communication with the interior volume of the balloon 65. A piece of sterile tape (not shown) may be applied to the exterior of the shaft 64 from the hub 66 to just inside the pleural cavity, thereby forming a closed suction circuit to drain the pleural cavity in a manner similar to that described above.

With either the applicator of FIG. 1A or 2A, once the balloon is properly located and inflated and the suction circuit established (if needed), radiotherapy is commenced. The planed therapy can be delivered in one dose application, or can be divided into fractions and spread out in time. One treatment is complete, the apparatus is removed, and any closing required is performed in a conventional manner.

Figure 3:
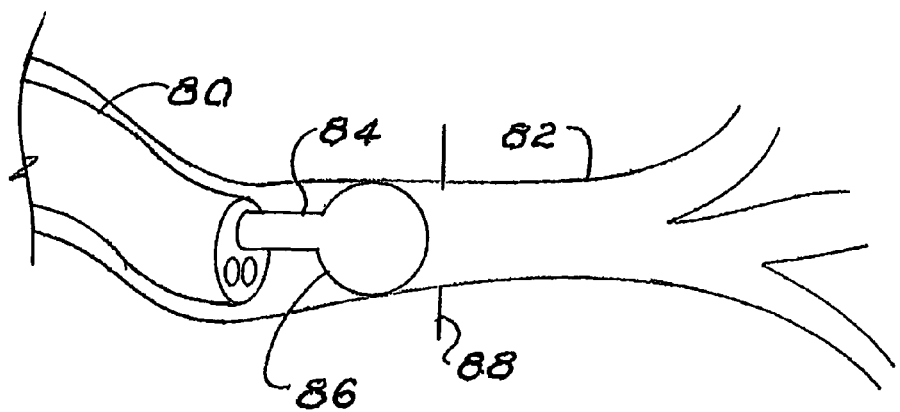
FIG. 3 is a schematic perspective view of a bronchoscope positioned within a section of bronchus, the bronchoscope having a intraluminal balloon applicator positioned and inflated within the resection portion of the bronchus.

FIG. 3 shows a bronchoscope 80 positioned in a portion of a bronchus 82 which has been resected and subsequently approximated. A balloon applicator 84 is shown protruding from the working channel of the bronchoscope 80, with the applicator balloon 86 inflated near the point of bronchus reapproximation 88. With bronchoscopic applications, the applicator shaft is preferably flexible so as easily to follow the working channel of the bronchoscope. A radiation source and flexible source catheter (neither shown) may be advanced into the balloon 86 from outside the patient, properly positioned, and radiotherapy commenced in accordance with a treatment plan.

Figure 4A:
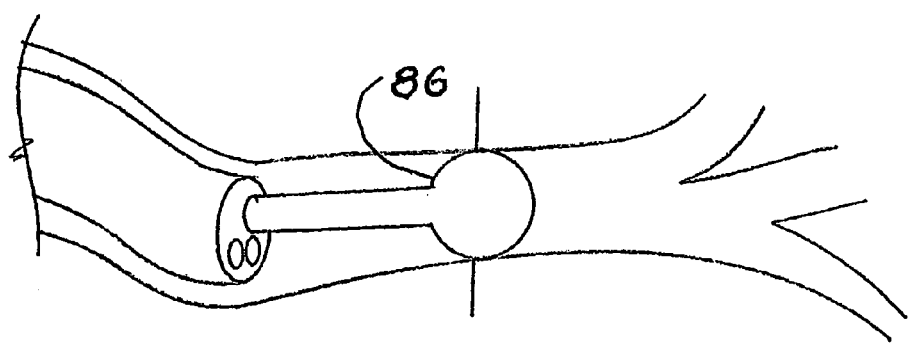
FIGS. 4A and B are progressive positions of an applicator similar to that of FIG. 3, but intended for multiple positioning within the bronchus being treated.
Figure 4B:
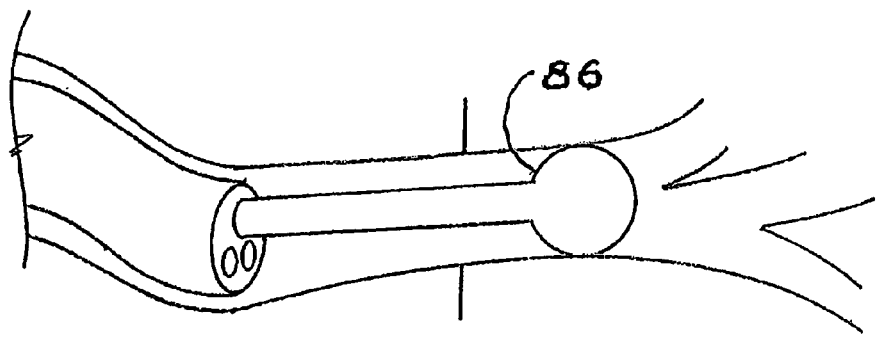
Figure 5:
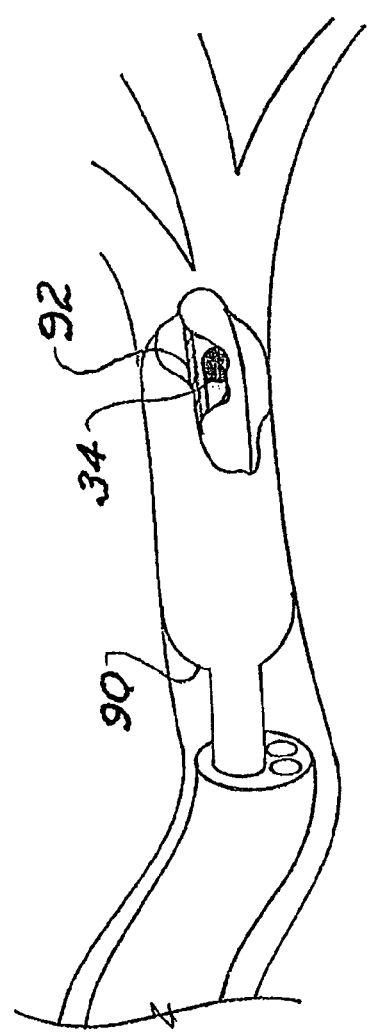
FIG. 5 is an schematic perspective view of an elongated balloon on a bronchial applicator of the invention, through which a radiation source may be translated in order to treat an elongated section of bronchus.

If desired in order to deliver radiotherapy to a longer section of bronchus, the balloon 86 may be deflated from its original position, moved within the bronchus, reinflated and further radiation delivered. Such stepping is illustrated in FIGS. 4A and 4B, and can be provided with use of a manipulator of the sort depicted in FIG. 3 of copending application Ser. No. 11/925,200 referenced herein. Because of the small scale of the bronchial anatomy, the eccentric source guides and methods of Ser. No. 11/925,200 may be advantageously utilized for treatment from within a balloon positioned in the bronchi. Alternatively to stepping, a sausage-shaped balloon 90 with two-point fastening to the shaft 92 may be used as depicted in FIG. 5. The hollow shaft 92 acts as a source guide for a source 34 which is translated within the balloon 90 in accordance with the treatment plan. After completion of treatment, the applicator and bronchoscope are removed.

With the methods and apparatus of this invention, the advantages of brachytherapy can be made available to virtually all patients undergoing surgery of the lung. Most notably, these advantages include less normal tissue exposure to radiation since no external radiation sources are used, fewer safety requirements to be observed (with x-ray tubes, no bunker facilities are required) and hence virtually any medical facility can perform the radiotherapy, and greatly reduced capital requirements and costs of treatment.

The above described preferred embodiments are intended to illustrate the principles of the invention, but not to limit its scope. Other embodiments and variations to these preferred embodiments will be apparent to those skilled in the art and may be made without departing from the spirit and scope of the invention as defined in the following claims.

We claim:

1. A method for brachytherapy treatment in a human lung, following resection of lung tissue, comprising:
    extending an applicator through the skin and visceral and the parietal pleura into the lung tissue and into a resection cavity, said applicator having an inflatable balloon at its distal end,
    the applicator having a shaft supporting the balloon, and defining an internal channel adapted to receive a catheter carrying a source of ionizing radiation near the distal end of the catheter, and the shaft including at a proximal end a hub through which the catheter can be inserted, and the hub including provision for inflating the balloon through the shaft,
    inflating the balloon within the resection cavity,
    irradiating tissue within the lung and adjacent to the resection cavity using the source carried by the catheter within the inflated balloon;
    following the step of irradiating tissue within the lung, deflating the balloon, withdrawing the applicator, and stitching or otherwise closing up any visceral and parietal pleura openings leading to the resection cavity and the skin;
    wherein the shaft includes a suction channel positioned to communicate via a suction circuit with a pleural cavity of the patient, to drain or evacuate fluid;
    wherein the applicator is partially withdrawn, followed by piercing or cutting a port in the suction channel.

2. The method of claim 1 wherein, once the port is pierced or cut in the suction channel, the applicator is inserted to a position wherein the port is in communication with the pleural cavity.

3. The method of claim 2, wherein, once the applicator is inserted, the balloon is inflated and the tissue is irradiated.

4. The method of claim 1, including closing the lung and the resection cavity around the applicator to generally seal against fluid leakage around the applicator.

5. The method of claim 1, wherein the shaft includes a suction port positioned to communicate via a suction circuit with a pleural cavity of the patient, to drain or evacuate fluid, and the method including withdrawing fluid from the pleural cavity to facilitate expansion of the lung.

6. The method of claim 1, wherein the suction circuit includes a slidable sleeve with the port, adjustable as to axial position, with the port positionable at the pleural cavity, and an evacuation port positioned on the sleeve to be exterior of the patient.

7. A method for brachytherapy treatment in a human lung, following resection of lung tissue, comprising:

extending an applicator through the skin into the lung tissue and into a resection cavity, said applicator having an inflatable balloon at its distal end, the applicator having a shaft supporting the balloon, and defining an internal channel adapted to receive a catheter carrying a source of ionizing radiation near the distal end of the catheter, and the shaft including at a proximal end a hub through which the catheter can be inserted, and the hub including provision for inflating the balloon through the shaft, inflating the balloon within the resection cavity, irradiating tissue within the lung and adjacent to the resection cavity using the source carried by the catheter within the inflated balloon;

the shaft including a suction channel positioned to communicate via a suction circuit with a pleural cavity of the patient, to drain or evacuate fluid; and partially withdrawing the applicator, followed by piercing or cutting a port in the suction channel.

8. The method of claim 7 wherein, once the port is pierced or cut in the suction channel, the applicator is inserted to a position wherein the port is in communication with the pleural cavity.

9. The method of claim 8, wherein, once the applicator is inserted, the balloon is inflated and the tissue is irradiated.

10. The method of claim 7 further including, following the step of irradiating tissue within the lung, deflating the balloon, fully withdrawing the applicator, and stitching or otherwise closing up the skin.

11. The method of claim 8 including blocking an end of the suction channel by a plug.

* * * * *